(12) United States Patent
Parodi

(10) Patent No.: US 6,497,670 B1
(45) Date of Patent: Dec. 24, 2002

(54) GUIDING DEVICE AND METHOD FOR INSERTING AND ADVANCING CATHETERS AND GUIDEWIRES INTO A VESSEL OF A PATIENT IN ENDOVASCULAR TREATMENTS

(76) Inventor: Juan Carlos Parodi, Blanco Encalada 1547, 1428 Capital Federal (AR)

( * ) Notice: Subject to any disclaimer, the term of this patent is extended or adjusted under 35 U.S.C. 154(b) by 0 days.

(21) Appl. No.: 09/526,573

(22) Filed: Mar. 16, 2000

Related U.S. Application Data

(63) Continuation of application No. 09/143,819, filed on Aug. 31, 1998, now Pat. No. 6,095,990.

(51) Int. Cl.[7] .................................................. A61B 5/00
(52) U.S. Cl. ...................................................... 600/585
(58) Field of Search .................... 660/433–436, 660/585

(56) References Cited

U.S. PATENT DOCUMENTS

| | | |
|---|---|---|
| 4,824,435 A | 4/1989 | Giesy et al. |
| 5,024,234 A | 6/1991 | Leary et al. |
| 5,040,548 A | 8/1991 | Yock |
| 5,102,403 A | 4/1992 | Alt |
| 5,147,377 A | 9/1992 | Sahota |
| 5,306,261 A | 4/1994 | Allman et al. |
| 5,344,413 A | 9/1994 | Allman et al. |
| 5,357,978 A | 10/1994 | Turk |
| 5,388,590 A | 2/1995 | Horrigan et al. |
| 5,395,332 A | 3/1995 | Ressemann et al. |
| 5,413,560 A | 5/1995 | Solar |
| 5,425,711 A | 6/1995 | Ressemann et al. |
| 5,449,362 A | 9/1995 | Chaisson et al. |
| 5,728,067 A | 3/1998 | Enger |

OTHER PUBLICATIONS

Copy of International Search Report dated Oct. 19, 1999.
Copy of Written Opinion dated Jul. 13, 2001.

Primary Examiner—Max Hindenburg
(74) Attorney, Agent, or Firm—RatnerPrestia

(57) ABSTRACT

A guiding device and method for inserting and advancing more than one catheter and/or guidewire through the vascular tree of a patient in endovascular treatments, particularly through tortuous blood vessels, the guiding device comprising an open or close guiding channel provided at a distal end of the catheter or guidewire, whereby the catheter or guidewire may be easily advanced through the vessel over a previously installed guidewire.

12 Claims, 2 Drawing Sheets

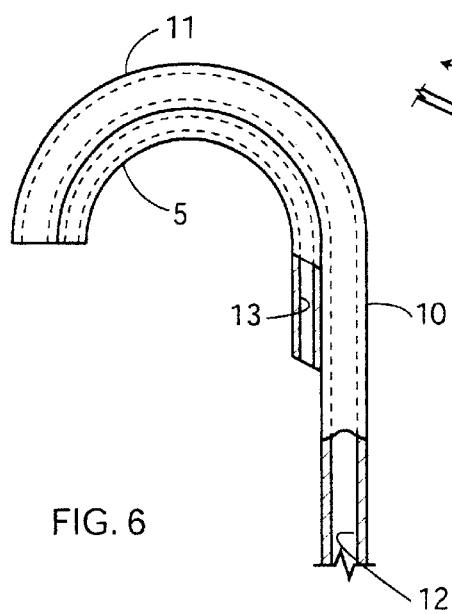
FIG. 6
FIG. 7
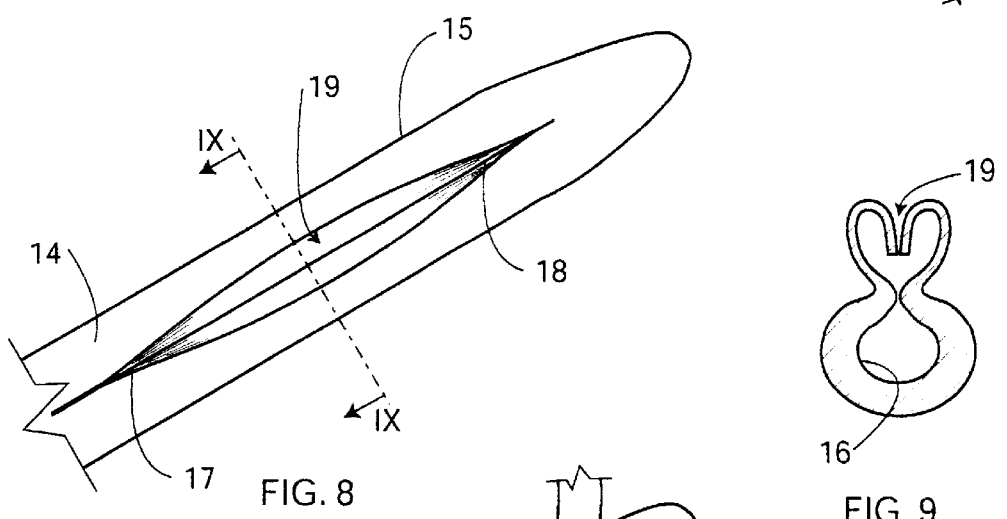
FIG. 8
FIG. 9
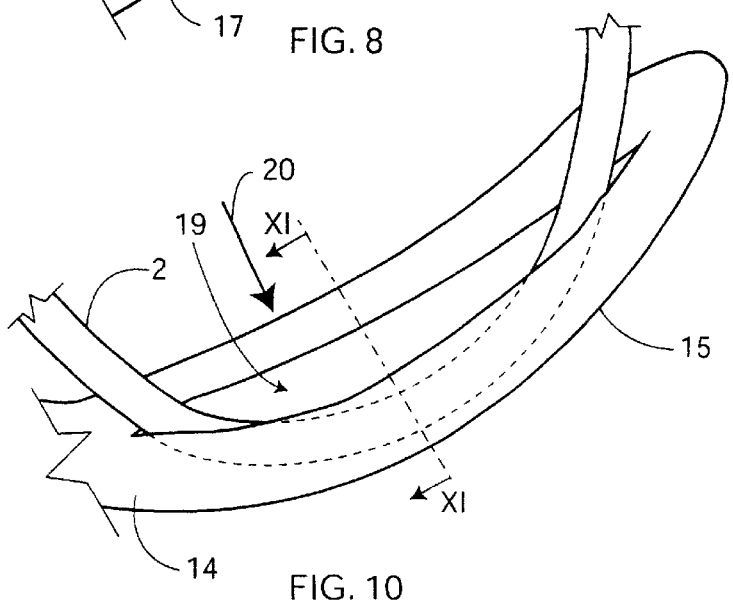
FIG. 10
FIG. 11

GUIDING DEVICE AND METHOD FOR INSERTING AND ADVANCING CATHETERS AND GUIDEWIRES INTO A VESSEL OF A PATIENT IN ENDOVASCULAR TREATMENTS

This application is a continuation U.S. patent application Ser. No. 09/143,819, filed on Aug. 31, 1998, now U.S. Pat. No. 6,095,990.

BACKGROUND OF THE INVENTION

1. Field of the Invention

The present invention relates to the field of endovascular treatments and, more particularly relates to a guiding device for helping in inserting and advancing catheters and/or guidewires into blood vessels of a patient during endovascular treatments, the invention also being related to a method for inserting and advancing such catheters and/or guidewires.

2. Description of the Prior Art

Angioplasty and other endovascular techniques are well know and broadly utilized medical processes consisting of inserting catheters and/or guidewires into the vascular tree of a patient with the purpose of reaching a remote blood vessel site having a lesion. The catheters and guidewires must be carefully maneuvered and steered through the patient's vessels until reaching the site of the lesion. A premise and basic requisite in the handling of these techniques is to provide an accurate and non-traumatic positioning of the catheters and guidewires in the desired vessel site and in the advancing of the wires and catheters along the vascular tree.

Under predetermined circumstances two guidewires need to be inserted into a blood vessel under treatment in order to have one of the guidewires located in the desired site. When two guidewires are used, the exchange of the guidewires is performed by advancing a catheter over a first guidewire that had been previously inserted and located into the vessel. Once the catheter has reached the desired area the first guidewire is removed and a second guidewire is advanced through a lumen of the catheter so as to have the first guidewire replaced by the second guidewire.

Once the second guidewire is in position, the catheter is removed to leave the second guidewire in the desired position. Then, a preloaded guidewire, either carrying a stent or a stent-graft, may be inserted into the vessel along the guidewire already in the vessel. This operation is carried out with the purpose of installing a stent or a graft in the site with the lesion.

The above operations may be extremely cumbersome when the blood vessel defines a tortuous path for the guidewires and catheters. When a guidewire or catheter must be advanced through a tortuous artery, a second guidewire, parallel to the first one, must be inserted into the blood vessel to make the vessel straight in order to facilitate the advancing of the pre-loaded guidewire. The advancing of the second guidewire, however, entails the same difficulties like the advancing of the first guidewire.

There is therefore need for a new and improved guidewire and/or catheter guiding system and method which can overcome these difficulties.

SUMMARY OF THE INVENTION

It is therefore one object of the present invention to provide a guiding device and method for inserting and advancing one or more than one catheter and/or guidewire through the vascular tree of a patient in endovascular treatments, particularly through tortuous blood vessels, the guiding device comprising an open or closed guiding channel provided at a distal end of the catheter or guidewire, whereby the catheter or guidewire may be easily advanced through the vessel over a previously installed guidewire.

It is still another object of the present invention to provide a guiding device for inserting and advancing more than one catheter and/or guidewire through the vascular tree of a patient in endovascular treatments, the device comprising a catheter shaft comprising a proximal end, a distal end and at least one fluid delivery lumen in fluid communication with the proximal end and the distal end, the distal end including a wire-guiding channel or conduit for slidably receiving a guiding wire whereby the catheter may be advanced through a vessel of the patient by slidably advancing the distal end of the catheter over the guiding wire.

It is a further object of the present invention to provide a guiding device for inserting and advancing one or more than one catheter and/or guidewire through the vascular tree of a patient in endovascular treatments, the device comprising a flexible conduit defining a main guidewire comprising a proximal end, a distal end and at least one lumen in fluid communication with the proximal end and the distal end, the distal end including a guiding channel for slidably receiving an additional guidewire whereby the main guidewire may be advanced through a vessel of the patient by slidably advancing the distal end over the additional guidewire.

It is even another object of the present invention to provide a guiding device for inserting and advancing one or more than one catheter and/or guidewire through the vascular tree of a patient in endovascular treatments, the device comprising a metal guidewire with a distal end and a proximal end, the distal end including a guiding channel for slidably receiving an additional guidewire whereby the metal guidewire may be advanced through a vessel of the patient by slidably advancing the distal end over the additional guidewire.

It is still another object of the present invention to provide a method for inserting and advancing one or more than one catheter and/or guidewire through the vascular system of a patient in endovascular treatments, the method comprising the steps of:

providing a catheter having a catheter shaft comprising a proximal end, a distal end and at least one fluid delivery lumen in fluid communication with the proximal end and the distal end, the distal end including a guiding channel for slidably receiving a guiding wire, inserting the guiding wire into the channel of the catheter, and advancing the catheter through a vessel of the patient by slidably advancing the distal end over the guiding wire.

It is even another object of the present invention to provide a method for inserting and advancing one or more than one catheter and/or guidewire through the vascular system of a patient in endovascular treatments, the method comprising the steps of:

providing a flexible conduit defining a guidewire comprising a proximal end, a distal end and at least one lumen in fluid communication with the proximal end and the distal end, the distal end including a guiding channel for slidably receiving a guiding wire, inserting the guiding wire into the channel of the flexible conduit, and advancing the flexible conduit through a vessel of the patient by slidably advancing the distal end over the guiding wire.

It is even another object of the present invention to provide a method for inserting and advancing one or more than one catheter and/or guidewire through the vascular tree of a patient in endovascular treatments, the method comprising the steps of:

providing a flexible metal guidewire comprising a proximal end and a distal end, the distal end including a guiding channel for slidably receiving an additional guidewire, inserting the additional guidewire into the guiding channel of the flexible metal guidewire, and advancing the metal guidewire through a vessel of the patient by slidably advancing the distal end over the additional guidewire.

The above and other objects, features and advantages of this invention will be better understood when taken in connection with the accompanying drawings and description.

BRIEF DESCRIPTION OF THE DRAWINGS

The present invention is illustrated by way of example in the following drawings wherein:

FIG. 6 shows a side elevation partial cross-sectional view of a distal end of a "Jockey" type catheter including the guiding system of the invention;

FIG. 7 shows a perspective view of a distal end of the "Jockey" type catheter of FIG. 6 including the guiding system of the present invention and running over a guidewire previously inserted into a blood vessel (not illustrated);

FIG. 8 shows a perspective view of a distal end of a catheter or guidewire including guiding system according to another embodiment of the invention;

FIG. 9 shows a cross-sectional view taken along line IX—IX of FIG. 8;

FIG. 10 shows a perspective view of a distal end of the catheter or guidewire of FIG. 8, with a guidewire being laterally inserted into the guiding system of the invention; and FIG. 11 shows a cross-sectional view taken along line XI—XI of FIG. 10;

DESCRIPTION OF THE PREFERRED EMBODIMENTS

Figure 1:
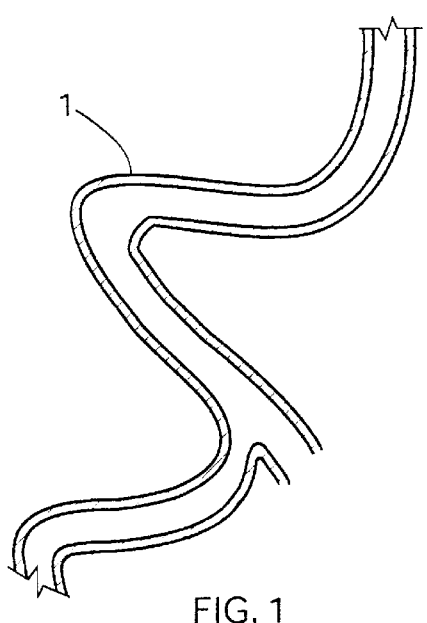
FIG. 1 shows a cross-sectional view of a blood vessel through which a catheter or a guidewire must be passed, the vessel having a tortuous path.
Figure 2:
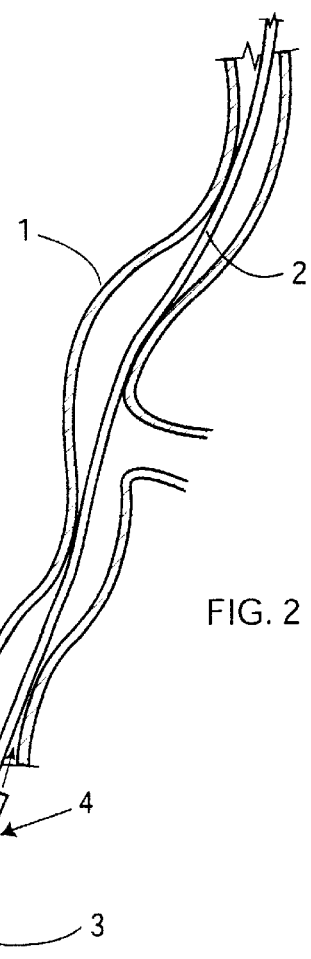
FIG. 2 shows a cross-sectional view of the blood vessel of FIG. 1, partially straightened by a guidewire inserted therein, with a second guidewire including the guiding system of the present invention and ready to be inserted into the vessel over the first, previously inserted guidewire.
Figure 3:
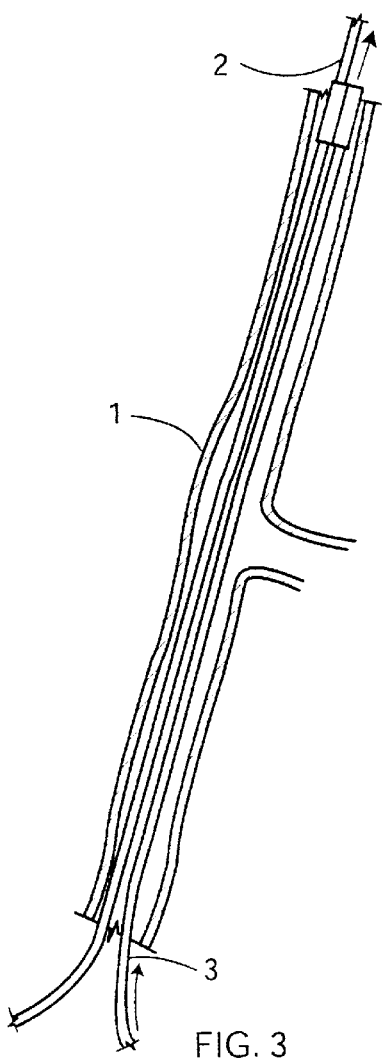
FIG. 3 shows a cross-sectional view of the blood vessel of FIGS. 1 and 2, straightened as desired by two guidewires inserted into the vessel by using one of the guidewires provided with the guiding system of the invention.

Now referring in detail to the drawings it may be seen from FIGS. 1–3 a tortuous blood vessel, like an artery 1 that is in the path for a catheter or a guidewire that must be inserted through the artery to reach a remote site of the vascular tree of a patient having a lesion to be treated by an endovascular process, for example. The object of the present invention is to provide a guiding system for a guidewire or a catheter that must be inserted into vessel 1 to facilitate the insertion of the catheter andor guidewire by making the vessel straightened through the method sequences shown in FIGS. 2, 3. As it is shown in FIG. 2, a guidewire 2 has been inserted through vessel 1 by any well known procedure and the vessel is partially straightened due to the wire remaining into the vessel. Even when the vessel is not so tortuous like in FIG. 1, the path necessary for advancing other guidewires or catheters, for instance a preloaded guidewire with a stent or a stent graft, is not clear enough as desired. Therefore, the vessel must be further treated to make it straight enough to proceed with the endovascular process. Thus, another guidewire 3 is inserted into the vessel, parallel to the first inserted guidewire 2. Guidewire 3, however, must be carefully maneuvered and steered into the vessel preventing the vessel from being damaged. According to the invention, a distal end 4 of guidewire 3 is provided with guiding means comprising a short channel or conduit 5 arranged on the outer surface of the guidewire. Although a conduit has been illustrated, also a ring, a groove or any other guiding channel may be provided.

According to a method of the invention, channel 5 is slidably advanced over guidewire 2, as indicated by the arrow, in order to place guidewire 3 parallel to guidewire 2, as it is shown in FIG. 3, and have the vessel straighten enough for further endovascular techniques to be carried out in the patient.

Figure 4:
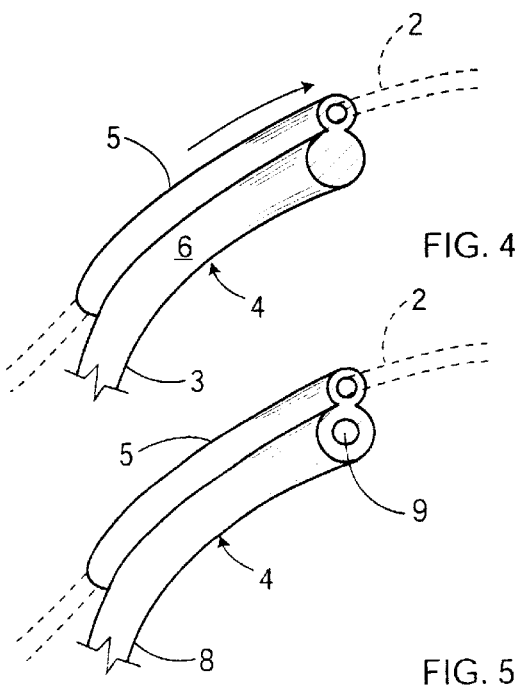
FIG. 4 shows a perspective partial cross-sectional view of a distal end of a guidewire including the guiding system of the invention.

Although reference has been made to a guidewire 3, a catheter can also be advanced over guidewire 2, as it will be seen later in connection to FIGS. 4, 5. FIG. 4 shows in more detail distal end 4 of guidewire 3. The distal end includes a short guiding channel, preferably a conduit 5, arranged on outer surface 6 of the guidewire. Guidewire 3 is a metal solid wire, while guiding conduit defines a path for slidably receiving guidewire 2 shown in phantom lines.

Figure 5:
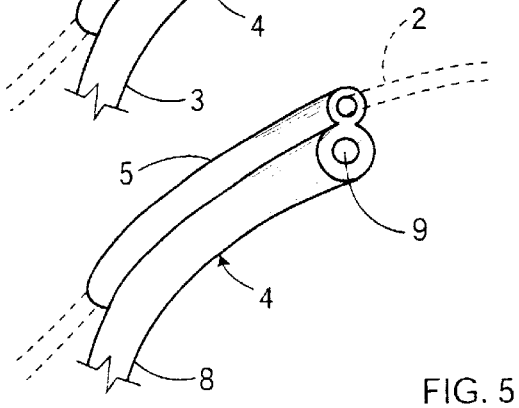
FIG. 5 shows a perspective partial cross-sectional view of a distal end of a catheter including the guiding system of the invention.

FIG. 5 shows the guiding system of the invention, preferably conduit 5, provided in a distal end 7 of a catheter 8, including a lumen 9 for carrying fluids or other medical tools. Conduit 5 is also slidably carried over guidewire 2 shown in phantom lines. Conduit 5 preferably has a length of 2 cm to 3 cm. Conduit 5 may be a closed conduit or may be longitudinally and laterally open, for instance with a longitudinal groove (not shown) to facilitate a side insertion of the conduit over guidewire 2. A further embodiment showing a side open groove applied to a catheter will be described in detail later in connection to FIGS. 8–10. The provision of such a groove makes it easier and faster to inset the guidewire into the guiding conduit.

FIGS. 6 and 7 show a catheter 10 having a curved distal end 11, also known as a "Jockey" type catheter, wherein the guiding means of the invention, also consisting of a guiding conduit 5 like the one illustrated in FIGS. 2–5, is provided. Catheter 10 has a lumen 12 and conduit 5 defines a channel 13 for passing a guidewire indicated by the same reference number 2 like in the other Figures. When conduit 5 is not open at its sides, the conduit must be inserted over the guidewire at a proximal end (not shown) of the guidewire 2. Otherwise, if a lateral or side groove is provided in the conduit, the latter may be inserted by pressure at any section over the guidewire.

FIGS. 8–11 show another embodiment of the invention wherein the guiding means are devised by means of a side groove for receiving the guidewire. A catheter 14 includes, at a distal end 15 thereof, the guiding means of the invention comprising a guiding channel defined by a short portion 16 of the lumen of the catheter with openings 17, 18 at respective ends of the channel portion. Thus, guiding channel 16 is open to one side of the catheter, forming a resilient groove 19 capable of receiving guiding wire 2 and resiliently retaining the guiding wire within lumen 16. As shown, groove 19 is in fluid communication with the lumen of the catheter and defines an entrance for the guidewire, the entrance being tangentially extended relative to an outer surface of the catheter.

Groove 19 provides at least one wide opening to the outside of the catheter or guidewire and becomes narrower as it comes into lumen 16 thus providing a safe retention of guidewire 2 within lumen 16, also thank to the resilient shape memory of these catheters and guidewires. Guidewire 2 must be inserted laterally to the catheter as indicated by arrow 20 in FIGS. 10 and 11, by applying a predetermined pressure in order to allow the guidewire to reach the main lumen of the catheter or the guidewire. Thus a groove may be provided either in a catheter or in a guidewire with a lumen like lumen 16.

The above method, however, may have a drawback. If two independent elements, such as a guidewire and a catheter or two guidewires, go through the valve of the introducer usually used in endovascular procedures, a blood leakage is very often generated through said valve. The solution to this potential cumbersome situation is to use a "Y" adapter advancing the two independent elements through each one of the adapter branches and then producing the liaison of the two independents elements before passing the valve of the introducer.

Also according to the invention, a method for inserting and advancing more than one catheter and/or guidewire through the vascular tree of a patient, is provided, preferably in endovascular processes. The method may be carried out with a guidewire and a catheter or with two guidewires.

When a catheter must be inserted into blood vessel 1, in addition to a previously inserted guidewire, the method comprises the steps of providing guidewire 3 (or catheter 8) having a catheter shaft comprising a proximal end, distal end 4(or 7) delivery lumen 9(or 12) in fluid communication with the proximal end and the distal end, the distal end including a guiding channel 5 for slidably receiving guiding wire 2, inserting the guiding wire into the channel of the catheter, and advancing the catheter through vessel 1 of the patient by slidably advancing the distal end over the guiding wire.

Once a guidewire has been inserted into vessel 1, another guidewire including the guiding means of the invention may be inserted according to the method of the invention.

When the guiding channel of the invention is provided with a side groove 19, the guiding channel does not need to be inserted over guidewire 2, at a proximal end of the guidewire, but guidewire may be inserted into the guide channel, as shown in FIG. 11, at any section of the guidewire, close to the patient's body.

When reference is made to an "open" or "closed" guiding channel or conduit in this specification, it means that the guiding channel or conduit is open at its ends to receive a guidewire but the side walls of the conduit or channel may be open to allow the guidewire to be sideway inserted by pressure into the conduit or channel.

While preferred embodiments of the present invention have been illustrated and described, it will be obvious to those skilled in the art that various changes and modifications may be made therein without departing from the scope of the invention as defined in the appended claims.

I claim:

1. A guiding device for inserting and advancing more than one guidewire and/or catheter through the vascular tree of a patient in endovascular treatments, the device comprising a metal guidewire with a distal end, a proximal end, and an outer diameter, the distal end including a guiding channel having a length for slidably receiving an additional guidewire whereby the metal guidewire may be advanced through a blood vessel of the patient by slidably advancing the distal end over the additional guidewire, the guiding channel having an inner diameter essentially no greater than necessary to accommodate the outer diameter of the additional guidewire.

2. The guiding device of claim 1, wherein the guiding channel is a conduit arranged on an outer surface of the metal guidewire.

3. The guiding device of claim 1 wherein the guiding channel comprises a resilient groove open to one side of the guiding channel, the resilient groove adapted for lateral insertion and resilient retention of the additional guidewire or catheter in the guiding channel.

4. A catheter for insertion and advancement over a guidewire through a vascular tree of a patient in an endovascular treatment, the catheter comprising a proximal end, a distal end a catheter lumen in fluid communication with the proximal end and the distal end, and a wire-guiding conduit arranged on an outer surface of the catheter at the distal end parallel to the catheter lumen over the entire length of the wire-guiding conduit and having a length for slidably receiving and peripherally surrounding a guiding wire, whereby the catheter may be advanced through a blood vessel of the patient by slidably advancing the wire-guiding conduit over the guiding wire, wherein the wire-guiding conduit comprises an inlet opening and an outlet opening on one side of the catheter adapted for entry and exit of the guiding wire into and out of the wire-guiding conduit, wherein the catheter forms, between the inlet opening and the outlet opening, a resilient groove adapted for lateral insertion and resilient retention of the guiding wire in the wire-guiding conduit.

5. The guiding device of claim 4 wherein the inlet opening and outlet opening are spaced apart from one another by 2–3 cm.

6. The guiding device of claim 4 wherein the groove defines a second lumen in fluid communication with the catheter lumen.

7. A method for inserting and advancing a catheter over a guidewire through a vascular tree of a patient in an endovascular treatment, the method comprising the steps of:

providing a catheter comprising a proximal end, a distal end, a lumen in fluid communication with the proximal end and the distal end, and a wire-guiding conduit arranged on an outer surface of the catheter at a distal end parallel to the catheter lumen over the entire length of the wire-guiding conduit and having a length for slidably receiving and peripherally surrounding the guidewire, the wire-guiding conduit comprising an inlet opening and an outlet opening on one side of the catheter adapted for entry and exit of the guidewire into and out of the wire-guiding conduit, wherein the catheter comprises, between the inlet opening and the outlet opening, a resilient groove adapted for lateral insertion and resilient retention of the guidewire in the guiding conduit;

laterally inserting the guidewire, having a proximal end and a distal end, in the inlet opening and out the outlet opening in the catheter at a point on the guidewire intermediate the proximal and distal ends of the guidewire;

advancing the catheter through a vessel of the patient by slidably advancing the wire-guiding conduit over the guidewire.

8. A method for straightening a tortuous blood vessel in an endovascular process, the method comprising the steps of:

inserting a first guidewire into the vessel;

inserting a second guidewire having an outer diameter into the vessel along the first guidewire into a position parallel to the first guidewire, thereby straightening the vessel, the second guidewire comprising a proximal end, a distal end and a first lumen in fluid communication with the proximal end and the distal end, the distal end including a wire-guiding channel having a length for slidably receiving and advancing along the first guidewire, wherein the guiding channel comprises one or both of: (a) a resilient groove open to one side of the guiding channel and adapted for lateral insertion and resilient retention of the first guidewire in the guiding channel, said groove defining a second lumen in fluid communication with said first lumen, (b) an inlet opening and an outlet opening on one side of the second guidewire adapted for entry and exit of the first guidewire in the guiding channel, the inlet opening, outlet opening, and guiding channel having a diameter essentially no greater than necessary to accommodate the outer diameter of the first guidewire.

9. A method for inserting and advancing more than one guidewire through a vascular system of a patient in an endovascular treatment, the method comprising the steps of:

providing a device comprising a metal guidewire with a distal end, a proximal end, and an outer diameter, the distal end including a wire-guiding channel having a length for slidably receiving an additional guidewire whereby the metal guidewire may be advanced through a blood vessel of the patient by slidably advancing the distal end over the additional guidewire, the guiding channel having an inner diameter essentially no greater than necessary to accommodate the outer diameter of the additional guidewire;

inserting the additional guidewire in the inlet opening and out the outlet opening of the wire-guiding channel in the metal guidewire; and advancing the metal guidewire through a vessel of the patient by slidably advancing the wire-guiding channel over the additional guidewire.

10. A method for straightening a tortuous blood vessel in an endovascular process, the method comprising the steps of:

inserting a guidewire into the vessel;

inserting a catheter into the vessel along the guidewire into a position parallel to the guidewire, thereby straightening the vessel, the catheter comprising a proximal end, a distal end and a first lumen in fluid communication with the proximal end and the distal end, the distal end including a wire-guiding channel having a length for slidably receiving and advancing along the guidewire, wherein the guiding channel comprises a resilient groove open to one side of the guiding channel and adapted for lateral insertion and resilient retention of the guidewire in the guiding channel, said groove defining a second lumen in fluid communication with the first lumen.

11. A method for inserting and advancing more than one catheter and/or guidewire through a vascular tree of a patient in an endovascular treatment, the method comprising the steps of:

providing a flexible metal guidewire comprising a proximal end, a distal end, and an outer diameter, the distal end including a guiding channel for slidably receiving an additionally guidewire or catheter, the guiding channel having an inner diameter essentially no greater than necessary to accommodate the outer diameter of the additional guidewire or catheter, inserting the additional guidewire or catheter into the guiding channel of the flexible metal guidewire, and advancing the metal guidewire through a vessel of the patient by slidably advancing the distal end over the additional guidewire or catheter.

12. The method of claim 11, wherein the guiding channel comprises a resilient groove open to one of the guiding channel and adapted for lateral insertion and resilient retention of the additional guidewire or catheter in the guiding channel, the additional guidewire or catheter has a proximal end and a distal end, and the method comprises laterally inserting the additional guidewire or catheter into the guide channel at a point on the additional guidewire or catheter intermediate the proximal end and the distal end of the additional guidewire or catheter.

* * * * *